(12) United States Patent
Kwon et al.

(10) Patent No.: US 8,450,502 B2
(45) Date of Patent: May 28, 2013

(54) PHARMACEUTICAL COMPOSITIONS FOR INHIBITING ANGIOGENESIS

(75) Inventors: Ho Jeong Kwon, Seoul (KR); Hye Jin Jung, Seoul (KR)

(73) Assignee: Industry-Academic Cooperation Foundation Yonsei University, Seoul (KR)

( * ) Notice: Subject to any disclaimer, the term of this patent is extended or adjusted under 35 U.S.C. 154(b) by 165 days.

(21) Appl. No.: 12/865,356

(22) PCT Filed: Jan. 30, 2009

(86) PCT No.: PCT/KR2009/000457
§ 371 (c)(1),
(2), (4) Date: Nov. 1, 2010

(87) PCT Pub. No.: WO2009/107933
PCT Pub. Date: Sep. 3, 2009

(65) Prior Publication Data
US 2011/0039919 A1    Feb. 17, 2011

(30) Foreign Application Priority Data

Feb. 1, 2008   (KR) .................. 10-2008-0010441

(51) Int. Cl.
*C07D 333/50*    (2006.01)
*A61P 35/00*     (2006.01)

(52) U.S. Cl.
USPC ............................ 549/41; 514/443

(58) Field of Classification Search
USPC .................... 514/443; 549/45, 41
See application file for complete search history.

(56) References Cited

U.S. PATENT DOCUMENTS 5,574,039 A     11/1996   Varney et al.
2006/0070135 A1  3/2006   Tremblay et al.

FOREIGN PATENT DOCUMENTS

WO   WO 2009016081 A2 *  2/2009

OTHER PUBLICATIONS

Houtman, J. J., FASEB, Breakthroughs in Bioscience, Angiogenesis, 2010.*

Silverman, R. B., The Organic Chemistry of Drug Design and Drug Action, Academic Press Inc., 1992, 19-22.*
Konig, W., Keil, J., Berichte der Deutschen Chemischen Gesellschaft [Abteilung] B: Abhandlungen, 1922, 55B, 2149-2155.*
Berichte der Deutschen Chemischen Gesellschaft [Abteilung] B: Abhandlungen, 1922, 55B, 2149-2155.*
International Search Report for International Application No. PCT/KR2009/000457.
Written Opinion of the International Searching Authority for International Application No. PCT/KR2009/000457.

* cited by examiner

*Primary Examiner* — Yong Chong
*Assistant Examiner* — Jason A Deck
(74) *Attorney, Agent, or Firm* — Alston & Bird LLP (57) ABSTRACT

Provided is a pharmaceutical composition for inhibiting angiogenesis, comprising a therapeutically effective amount of a compound represented by Formula 1: (I) wherein R1 through R13 and X are as defined in the specification. Compounds used as an active ingredient in the pharmaceutical composition of the present invention bind to QP-C to provide effective prevention of angiogenesis and can be effectively used for prevention and/or treatment of angiogenesis-related diseases or disorders. Further, the active compounds of the present invention inhibit biological functions of QP-C, which consequently leads to inhibition of angiogenic responses without the risk of cellular apoptosis, thus significantly improving safety of the drug.

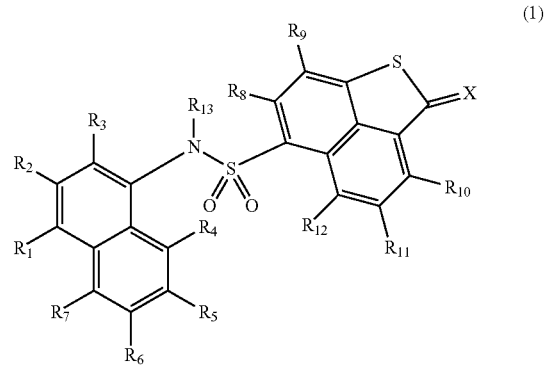

7 Claims, 5 Drawing Sheets

Figure 1

```
ATG GCT GGT AAG CAG GCC GTT TCA GCA TCA GGC AAG TGG CTG GAT GGT
Met Ala Gly Lys Gln Ala Val Ser Ala Ser Gly Lys Trp Leu Asp Gly
ATT CGA AAA TGG TAT TAC AAT GCT GCA GGA TTC AAT AAA CTG GGG TTA
Ile Arg Lys Trp Tyr Tyr Asn Ala Ala Gly Phe Asn Lys Leu Gly Leu
ATG CGA GAT GAT ACA ATA TAC GAG GAT GAA GAT GTA AAA GAA GCC ATA
Met Arg Asp Asp Thr Ile Tyr Glu Asp Glu Asp Val Lys Glu Ala Ile
AGA AGA CTT CCT GAG AAC CTT TAT AAT GAC AGG ATG TTT CGC ATT AAG
Arg Arg Leu Pro Glu Asn Leu Tyr Asn Asp Arg Met Phe Arg Ile Lys
AGG GCA CTG GAC CTG AAC TTG AAG CAT CAG ATC TTG CCT AAA GAG CAG
Arg Ala Leu Asp Leu Asn Leu Lys His Gln Ile Leu Pro Lys Glu Gln
TGG ACC AAA TAT GAA GAG GAA AAT TTC TAC CTT GAA CCG TAT CTG AAA
Trp Thr Lys Tyr Glu Glu Glu Asn Phe Tyr Leu Glu Pro Tyr Leu Lys
GAG GTT ATT CGG GAA AGA AAA GAA AGA GAA GAA TGG GCA AAG AAG
Glu Val Ile Arg Glu Arg Lys Glu Arg Glu Glu Trp Ala Lys Lys
```

| VEGF | - | + | + | + |
| HDNT (μM) | - | - | 2.5 | 5 |

Figure 4

| VEGF | - | + | + | + |
| HDNT (μM) | - | - | 2.5 | 5 |

Figure 5

HDNT (μM)

SEQUENCE LISTING

<160> NUMBER OF SEQ ID NOS: 2

<210> SEQ ID NO 1
<211> LENGTH: 333

```
<212> TYPE: DNA
<213> ORGANISM: Artificial Sequence
<220> FEATURE:
<223> OTHER INFORMATION: Phage-encoding sequence of human QP-C in
      QP-C-expressing bacteriophage T7

<400> SEQUENCE: 1
atggctggta agcaggccgt ttcagcatca ggcaagtggc tggatggtat tcgaaaatgg    60
tattacaatg ctgcaggatt caataaactg gggttaatgc gagatgatac aatatacgag   120
gatgaagatg taaaagaagc cataagaaga cttcctgaga acctttataa tgacaggatg   180
tttcgcatta agagggcact ggacctgaac ttgaagcatc agatcttgcc taagagcag    240 tggaccaaat atgaagagga aaatttctac cttgaaccgt atctgaaaga ggttattcgg   300
gaaagaaaag aaagagaaga atgggcaaag aag                                333

<210> SEQ ID NO 2
<211> LENGTH: 111
<212> TYPE: PRT
<213> ORGANISM: Artificial Sequence
<220> FEATURE:
<223> OTHER INFORMATION: Amino acid sequence of human QP-C in
      QP-C-expressing bacteriophage T7

<400> SEQUENCE: 2

Met Ala Gly Lys Gln Ala Val Ser Ala Ser Gly Lys Trp Leu Asp Gly
1               5                   10                  15

Ile Arg Lys Trp Tyr Tyr Asn Ala Ala Gly Phe Asn Lys Leu Gly Leu
            20                  25                  30

Met Arg Asp Asp Thr Ile Tyr Glu Asp Glu Asp Val Lys Glu Ala Ile
        35                  40                  45

Arg Arg Leu Pro Glu Asn Leu Tyr Asn Asp Arg Met Phe Arg Ile Lys
    50                  55                  60

Arg Ala Leu Asp Leu Asn Leu Lys His Gln Ile Leu Pro Lys Glu Gln
65                  70                  75                  80

Trp Thr Lys Tyr Glu Glu Glu Asn Phe Tyr Leu Glu Pro Tyr Leu Lys
                85                  90                  95

Glu Val Ile Arg Glu Arg Lys Glu Arg Glu Glu Trp Ala Lys Lys
            100                 105                 110
```

PHARMACEUTICAL COMPOSITIONS FOR INHIBITING ANGIOGENESIS

TECHNICAL FIELD

The present invention relates to a pharmaceutical composition for inhibiting angiogenesis.

BACKGROUND ART

Angiogenesis is required for development of solid tumors. Mitochondrial function is linked to angiogenesis, because mitochondria are major sites of oxygen consumption and angiogenesis is an oxygen concentration-sensitive process (Andreyev, A. Y., Kushnareva, Y. E., and Starkov, A. A. (2005). Mitochondrial metabolism of reactive oxygen species. Biochemistry (Mosc.) 70, 200-214; and Maulik, N., and Das, D. K. (2002). Redox signaling in vascular angiogenesis. Free Radic. Biol. Med. 33, 1047-1060). Further, it is known that changes in the mitochondrial redox state stimulate production of reactive oxygen species (ROS) during hypoxia and mitochondrial ROS activate transcription of proangiogenic proteins (Chandel, N. S., Maltepe, E., Goldwasser, E., Mathieu, C. E., Simon, M. C., and Schumacker, P. T. (1998). Mitochondrial reactive oxygen species trigger hypoxia-induced transcription. Proc. Natl. Acad. Sci. USA 95, 11715-11720). According to articles published in scientific journals, production of ROS at the mitochondrial complex III is a necessary and sufficient condition for triggering of HIF-1α stabilization during hypoxia (Brunelle, J. K., Bell, E. L., Quesada, N. M., Vercauteren, K., Tiranti, V., Zeviani, M., Scarpulla, R. C., and Chandel, N. S. (2005). Oxygen sensing requires mitochondrial ROS but not oxidative phosphorylation. Cell Metab. 1, 409-414; Chandel, N. S., McClintock, D. S., Feliciano, C. E., Wood, T. M., Melendez, J. A., Rodriguez, A. M., and Schumacker, P. T. (2000). Reactive oxygen species generated at mitochondrial complex III stabilize hypoxia-inducible factor-1 during hypoxia. J. Biol. Chem. 275, 25130-25138; Guzy, R. D., Hoyos, B., Robin, E., Chen, H., Liu, L., Mansfield, K. D., Simon, M. C., Hammerling, U., and Schumacker, P. T. (2005). Mitochondrial Complex III is required for hypoxia-induced ROS production and cellular oxygen sensing. Cell Metab. 1, 401-408; and Mansfield, K. D., Guzy, R. D., Pan, Y., Young, R. M., Cash, T. P., Schumacker, P. T., and Simon, M. C. (2005). Mitochondrial dysfunction resulting from loss of cytochrome c impairs cellular oxygen sensing and hypoxic HIF-alpha activation. Cell Metab. 1, 393-399). Cells deficient in mitochondrial DNA and electron transport activity (ρo cells) exhibit no increase of ROS or no upregulation of HIF-1α target genes during hypoxia. Complex III inhibitors suppress mitochondrial ROS production during hypoxia and inhibit stabilization and transcriptional activity of HIF-1α. These findings suggest that ROS production at the mitochondrial complex III is a crucial event in signaling of cellular hypoxia. From the fact that structural components of the mitochondrial complex III take part in cellular oxygen sensing, it is believed that low-molecular weight compounds inhibiting such a cellular oxygen-sensing pathway will be useful means for inhibition of hypoxia-induced angiogenesis.

Meanwhile, biological screening tools are useful for identification of natural compounds capable of inducing alterations of certain phenotypic traits (Kwon, H. J. (2003). Chemical genomics-based target identification and validation of anti-angiogenic agents. Curr. Med. Chem. 10, 717-726; and Liu, J., Farmer, J. D. Jr., Lane, W. S., Friedman, J., Weissman, I., and Schreiber, S. L. (1991). Calcineurin is a common target of cyclophilin-cyclosporin A and FKBP-FK506 complexes. Cell 66, 807-815). In order to find compounds capable of inhibiting angiogenic responses in response to proangiogenic stimuli (such as hypoxia) in endothelial cells, the present inventors extensively conducted large-scale screening of microbial extracts. As a result, the present inventors succeeded in identification of bicyclo sesterterpene, e.g. terpestacin and found that terpestacin is a candidate material capable of inhibiting angiogenic responses at a concentration below a toxic threshold (Jung, H. J., Lee, H. B., Kim, C. J., Rho, J. R., Shin, J., and Kwon, H. J. (2003). Anti-angiogenic activity of terpestacin, a bicyclo sesterterpene from *Embellisia chlatnydospora*. J. Antibiotics 56, 492-496).

Terpestacin strongly inhibits angiogenic responses of human umbilical vein endothelial cells (HUVEC) in vitro, and strongly inhibits angiogenesis of embryonic chick chorioallantoic membrane (CAM) in vivo. Further, terpestacin is known to inhibit the formation of syncytium during HIV infections and can be chemically synthesized (Chan, J., and Jamison, T. F. (2004). Enantioselective synthesis of (−)-terpestacin and structural revision of siccanol using catalytic stereoselective fragment couplings and macrocyclizations. J. Am. Chem. Soc. 126, 10682-10691; Myers, A. G., Siu, M., and Ren, F. (2002). Enantioselective synthesis of (−)-terpestacin and (−)-fusaproliferin: clarification of optical rotational measurements and absolute configurational assignments establishes a homochiral structural series. J. Am. Chem. Soc. 124, 4230-4232; and Oka, M., Iimura, S., Tenmyo, O., Sawada, Y., Sugawara, M., Ohkusa, N., Yamamoto, H., Kawano, K., Hu, S. L., Fukagawa, Y., and Oki, T. (1993). Terpestacin, a new syncytium formation inhibitor from *Arthrinium* sp. J. Antibiotics 46, 367-373).

The mitochondrial complex III consists of eleven protein subunits. Essential components of the complex III, e.g. cytochrome b, cytochrome c1, Rieske iron-sulfur protein and ubiquinone are functionally well understood (Crofts, A. R., and Berry, E. A. (1998). Structure and function of the cytochrome bc1 complex of mitochondria and photosynthetic bacteria. Curr. Opin. Struct. Biol. 8, 501-509; and Smith, J. L., Zhang, H., Yan, J., Kurisu, G., and Cramer, W. A. (2004). Cytochrome bc complexes: a common core of structure and function surrounded by diversity in the outlying provinces. Curr. Opin. Struct. Biol. 14, 432-439). In addition, specific inhibitors, for example, antimycin A, stigmatellin and myxothiazol have been widely used in functional studies of the complex III (Xia, D., Yu, C. A., Kim, H., Xia, J. Z., Kachurin, A. M., Zhang, L., Yu, L., and Deisenhofer, J. (1997). Crystal structure of the cytochrome bc1 complex from bovine heart mitochondria. Science 277, 60-66; Zhang, Z., Huang, L., Shulmeister, V. M., Chi, Y. I., Kim, K. K., Hung, L. W., Crofts, A. R., Berry, E. A., and Kim, S. H. (1998). Electron transfer by domain movement in cytochrome bc1. Nature 392, 677-684). Unfortunately, these compounds are not suitable as inhibitors of tumor angiogenesis, because they exhibit disadvantages such as inhibition of electron transport, abolition of oxidative phosphorylation, and induction of cellular apoptosis. For these reasons, there is a need for development of novel compounds deleting oxygen sensing functions of the complex III while not causing disruption of ATP production. Therefore, this is attracting a great deal of interest particularly from cancer biologists who have been focused on inhibition of adaptive responses (for example, expression of vascular endothelial growth factor) to hypoxia.

Throughout the specification, numerous scientific articles and patent publications are cited and citations thereof are identified. Disclosures of the cited articles and patent references are incorporated by reference herein in their entirety, such that a current status of a technical field to which the present invention pertains and the disclosure of the present invention will be more clearly described.

DISCLOSURE

Technical Problem

As a result of a variety of extensive and intensive studies and experiments to solve the problems as described above and develop an effective anti-angiogenic agent, the inventors of the present invention succeeded in finding a novel anti-angiogenic agent intended to target a ubiquinone-binding protein (QP-C) of a mitochondrial complex III, as a molecular target for angiogenesis, and discovered that such an anti-angiogenic agent binds to QP-C to result in effective blockade of angiogenesis. The present invention has been completed based on these findings.

Therefore, the present invention has been made in view of the above problems, and it is an object of the present invention to provide a pharmaceutical composition for inhibiting angiogenesis.

The above and other objects, features and other advantages of the present invention will be more clearly understood from the following detailed description taken in conjunction with the accompanying drawings and claims.

Technical Solution

In accordance with an aspect of the present invention, the above and other objects can be accomplished by the provision of a pharmaceutical composition for inhibiting angiogenesis, comprising:

(a) a therapeutically effective amount of a compound represented by Formula 1:

(1)

wherein R1 to R12 are each independently hydrogen, halo, hydroxy, cyano, amino, nitro, nitroso, carboxyl, C1-C12 alkyl, C2-C6 alkenyl, C3-C8 cycloalkyl, C5-C7 cycloalkenyl, C 1-C6 alkylamino, C1-C6 alkoxy, aryl, heteroaryl, arylalkyl, arylalkenyl or alkylaryl; R13 is hydrogen, hydroxy, C1-C12 alkyl or C1-C6 alkoxy; and X is oxygen or sulfur; and (b) a pharmaceutically acceptable carrier.

The present inventors made efforts to develop an effective anti-angiogenic agent. As a result, the present inventors succeeded in finding a novel anti-angiogenic agent intended to target a ubiquinone-binding protein (QP-C) of a mitochondrial complex III, as a novel molecular target in angiogenesis, and discovered that the novel anti-angiogenic agent binds to QP-C to provide effective prevention of angiogenesis.

The composition of the present invention is expressed in the term "pharmaceutical composition for inhibiting angiogenesis" which may be used interchangeably with the term "pharmaceutical composition for prevention or treatment of angiogenesis-related diseases" or "pharmaceutical composition for prevention or treatment of uncontrolled angiogenesis-related diseases". A compound used as an active ingredient in the pharmaceutical composition of the present invention is represented by Formula 1. The compound of the present invention has basically a naphthalene and naphthothiophene structure and contains a dioxysulfone group.

In Formula 1 that defines the compound of the present invention, the term "halo" refers to a halogen atom and includes, for example, fluoro, chloro, bromo and iodo. As used herein, the term "C1-C12 alkyl" refers to a C1-C12 linear or branched saturated hydrocarbon group, preferably "C1-C4 linear or branched alkyl", which is lower alkyl and includes methyl, ethyl, n-propyl, isopropyl, isobutyl, n-butyl and t-butyl. The term "alkenyl" refers to a linear or branched unsaturated hydrocarbon group having a specified number of carbon atoms, preferably C2-C6 linear or branched alkenyl, which is a C2-6 hydrocarbon group having at least one double bond and includes, for example, ethenyl, propenyl, isopropenyl, butenyl, isobutenyl, t-butenyl, n-pentenyl and n-hexenyl.

The term "cycloalkyl" refers to a cyclic hydrocarbon radical having a specified number of carbon atoms, preferably "C3-C8 cycloalkyl", which includes cyclopropyl, cyclobutyl and cyclopentyl. The term "cycloalkenyl" refers to a cyclic hydrocarbon group having a specified number of carbon atoms and at least one double bond, preferably "C5-C7 cycloalkenyl", which includes cyclopentene, cyclohexene and cyclohexadiene. The term "alkylamino" refers to an alkyl group having an amino substituent. The term "alkoxy" refers to —Oalkyl.

The term "aryl" refers to a completely or partially unsaturated, substituted or unsubstituted monocyclic or polycyclic carbon ring, preferably monoaryl or biaryl. Monoaryl preferably has 5 to 6 carbon atoms, and biaryl preferably has 9 to 10 carbon atoms. Most preferably, the aryl is substituted or unsubstituted phenyl. When monoaryl, for example phenyl, is substituted, it may be substituted by numerous substituents at various positions. Preferably, the substituent may be selected from the group consisting of halo, hydroxy, nitro, cyano, substituted or unsubstituted, linear or branched C1-C4 alkyl, linear or branched C1-C4 alkoxy, alkyl-substituted sulfanyl, phenoxy, C3-C6 cycloheteroalkyl and substituted or unsubstituted amino.

The term "heteroaryl" refers to a heterocyclic aromatic group which contains a heteroatom, for example N, O or S. Preferably, heteroaryl is heterobiaryl containing N as a heteroatom.

The term "arylalkyl (aralkyl)" refers to an aryl group attached to a structure consisting of one or more alkyl groups, preferably benzyl. The term "alkylaryl" refers to an alkyl group attached to a structure consisting of one or more aryl groups. The term "arylalkenyl" refers to an aryl group attached to a structure consisting of one or more alkenyl groups, preferably phenyl ethenyl.

In the preferred compound of the present invention, R1 is hydrogen, hydroxy, C1-C12 alkyl or C1-C6 alkoxy, more preferably hydroxy or C1-C6 alkoxy, and most preferably hydroxy.

In the preferred embodiment of the present invention, R2 to R12 are each independently hydrogen, hydroxy, C1-C12 alkyl, or C1-C6 alkoxy, more preferably are each independently hydrogen, hydroxy or C1-C12 alkyl, and most preferably hydrogen.

In the preferred embodiment of the present invention, R13 is hydrogen or hydroxy, and more preferably hydrogen.

In Formula 1, an oxygen or sulfur atom may be located at the position X. Most preferred is an oxygen atom.

In the most preferred embodiment of the present invention, R1 in Formula 1 is hydroxy, R2 to R12 are each independently hydrogen, R13 is hydrogen, and X is oxygen. The above-defined compound is 6-((1-hydroxynaphthalen-4-ylamino) dioxysulfone)-2H-naphtho[1,8-bc]thiophen-2-one (HDNT).

Diseases, disorders or conditions that can be prevented or treated by the pharmaceutical composition of the present invention include a variety of diseases associated with angiogenesis. Preferably, examples of diseases that can be prevented or treated by the composition of the present invention may include cancer, diabetic retinopathy, retinopathy of prematurity, age related macular degeneration (AMD), corneal graft rejection, neovascular glaucoma, erythema, proliferative retinopathy, psoriasis, hemophiliac joints, capillary proliferation within atherosclerotic plaques, keloids, wound granulation, vascular adhesions, rheumatoid arthritis, osteoarthritis, autoimmune diseases, Crohn's disease, restenosis, atherosclerosis, intestinal adhesions, cat scratch disease, ulcers, liver cirrhosis, glomerulonephritis, diabetic nephropathy, malignant nephrosclerosis, thrombotic microangiopathy, organ transplant rejection, glomerulopathy, diabetes, inflammation and neurodegenerative diseases.

Examples of autoimmune diseases that can be prevented or treated by the composition of the present invention may include, but are not limited to, alopecia greata, ankylosing spondylitis, antiphospholipid syndrome, autoimmune Addison's disease, autoimmune adrenal disease, autoimmune hemolytic anemia, autoimmune hepatitis, autoimmune ovaritis and testitis, autoimmune thrombocytopenia, Behcet's disease, Bullous pemphigoid, cardiomyopathy, celiac sprue-dermatitis, chronic fatigue immune dysfunction syndrome, chronic inflammatory demyelinating polyradiculoneuropathy, Churg-Strauss syndrome, cicatricial pemphigoid, CREST syndrome, cold agglutinin disease, Crohn's disease, discoid lupus, essential mixed cryoglobulinemia, fibromyalgia-fibromyositis, glomerulonephritis, Grave's disease, Guillain-Barre syndrome, Hashimoto's thyroiditis, idiopathic pulmonary fibrosis, idiopathic thrombocytopenic purpuras, IgA nephropathy, juvenile arthritis, lichen planus, lupus erythematosus, Meniere's disease, mixed connective tissue disease, multiple sclerosis, type I or immune-mediated diabetes, myasthenia gravis, pemphigus vulgaris, pernicious anemia, polyarteritis nodosa, polychondritis, autoimmune polyglandular syndrome, polymyalgia rheumatica, polymyositis and dermatomyositis, primary agammaglobulinemia, primary biliary cirrhosis, psoriasis, psoriatic arthritis, Raynaud's phenomenon, Reiter's syndrome, rheumatoid arthritis, Sarcoidosis, scleroderma, stiff-person syndrome, systemic lupus erythematosus, lupus erythematosus, Takayasu's arteritis, temporal arteritis, giant cell arteritis, ulcerative colitis, uveitis, vitiligo and Wegener's granulomatosis.

Examples of inflammatory diseases that can be prevented or treated by the composition of the present invention may include, but are not limited to, asthma, encephilitis, inflammatory enteritis, chronic obstructive pulmonary disease, allergy, septic shock, pulmonary fibrosis, undifferentiated spondyloarthropathy, undifferentiated arthropathy, arthritis, inflammatory osteolysis, and chronic inflammation by chronic viral or bacterial infections.

More preferably, the disease that can be prevented or treated by the pharmaceutical composition of the present invention may be cancer or diabetic retinopathy and age related macular degeneration (AMD).

As used herein, the term "therapeutically effective amount" refers to an amount which is sufficient to obtain desired efficacy or activity of a compound of Formula 1.

When the composition of the present invention is formulated into a pharmaceutical composition, the pharmaceutical composition may comprise one or more pharmaceutically acceptable carriers. The pharmaceutically acceptable carriers that can be used in the present invention may be materials conventionally used in formulations, and include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate and mineral oil. The pharmaceutical composition may further comprise lubricants, wetting agents, sweeteners, flavoring agents, emulsifiers, suspending agents, preservatives and the like, in addition to the above-mentioned ingredients. Details of suitable pharmaceutically acceptable carriers and preparations can be found in Remington's Pharmaceutical Sciences (19th ed., 1995).

The pharmaceutical composition may be conventionally administered by oral or parenteral routes known in the art. Examples of parenteral routes may include intravenous, subcutaneous, intramuscular, intraperitoneal, transdermal, intramucosal and intraocular injections.

As will be apparent to those skilled in the art, the effective dose of the pharmaceutical composition of the present invention may vary depending on various factors such as formulation methods, administration manners, age, weight, sex, pathological conditions, and dietary habits of patients, treatment duration, administration routes, excretion rates and response sensitivity. Preferably, the pharmaceutical composition of the present invention may be administered at a dose of 0.0001 to 100 mg/kg (BW)/day for adults.

The pharmaceutical composition of the present invention may be formulated into unit dosage forms, e.g., in multi-dose containers, using one or more pharmaceutically acceptable carriers and/or excipients, according to a method that can be easily practiced by one of ordinary skill in the art to which the invention pertains. The formulations may take such forms as solutions, suspensions, syrups or emulsions in oily or aqueous media, or extracts, powders, granules, tablets, or capsules and may further contain formulatory agents such as dispersing agents or stabilizing agents.

The pharmaceutical composition of the present invention arrests biological functions of QP-C to thereby inhibit the oxygen-sensing function of the mitochondrial complex III without disruption of ATP production, resulting in effective inhibition of angiogenesis in a safe manner to the human body. Therefore, the pharmaceutical composition of the present invention can be used for prevention and/or treatment of various angiogenesis-related diseases or disorders.

ADVANTAGEOUS EFFECTS

Features and advantages of the present invention are summarized as follows:

(i) The compounds used as an active ingredient in the pharmaceutical composition of the present invention bind to QP-C to result in effective prevention of angiogenesis.

(ii) The pharmaceutical composition of the present invention can be effectively used for prevention and/or treatment of angiogenesis-related diseases or disorders.

(iii) The compounds used as an active ingredient in the pharmaceutical composition of the present invention specifically bind to QP-C to result in inhibition of biological functions thereof. This consequently leads to inhibition of angiogenic responses without causing cellular apoptosis, thus significantly improving safety of the drug.

MODE FOR INVENTION

Now, the present invention will be described in more detail with reference to the following examples. These examples are provided only for illustrating the present invention and should not be construed as limiting the scope and spirit of the present invention.

Materials and Methods

Materials

Terpestacin was purified from an extract of fungus *Embellisia chlamydospora* (Jung, H. J., et al., Anti-angiogenic activity of terpestacin, a bicyclo sesterterpene from *Embellisia chlamydospora*, J. Antibiotics 56: 492-496 (2003)). HDNT [6-((1-hydroxynaphthalen-4-ylamino)dioxysulfone)-2H-naphtho [1,8-bc]thiophen-2-one] was purchased from SPECS®.

Synthesis of Molecular Probe for Terpestacin (1) Biotinylated Terpestacin 1-(3-dimethylaminopropyl)-3-ethylcarbodiimide (EDC) (1.5 mg 0.0078 mmol, SIGMA-ALDRICH®) and 4-dimethylaminopyridine (DMAP) (1.0 mg, 0.0082 mmol, SIGMA-ALDRICH®) were added to a stirred solution of terpestacin (3.0 mg, 0.0075 mmol), and N-(+)-biotinyl-6-aminohexanoic acid (2.7 mg, 0.0076 mmol, Pierce Biotechnology, Inc) in DMSO (3 mL) was added thereto at 0° C. The reaction mixture was reacted overnight at room temperature. The reaction product was extracted with ethanol (15 mL) and purified by TLC ($CH_2Cl_2$:MeOH=10:1) to obtain two biotinylated terpestacin derivatives (hydroxyl at C-24 [BT1] and hydroxyl at C-17[BT2]). Yield: 75%.

MALDI-MS for $C_{41}H_{63}N_3O_7S$ m/z 764.5 $[M+Na]^+$.

(2)

BT1

(3)

BT2

(2) Coumarin-conjugated Terpestacin

EDC (1.0 mg, 0.0052 mmol) and DMAP (0.64 mg, 0.0052 mmol) were added to a stirred solution of terpestacin (2.0 mg, 0.005 mmol) and Boc-6-aminohexanoic acid (1.2 mg, 0.0052 mmol) in DMF (2 mL) at 0° C. The reaction mixture was reacted overnight at room temperature. The reaction product was extracted with ethanol (4 mL×3), treated with 20% TFA in $CH_2Cl_2$ (1 mL) and stirred at room temperature for 2 hours. DIPEA (1.3 mg, 0.01 mmol) and 6-((7-amino-4-methylcoumarin-3-acetyl)amino)hexanoic acid succinimidyl ester (2.2 mg, 0.005 mmol, MOLECULAR PROBES®) were added thereto at 0° C. After being stirred at room temperature for 4 hours, the reaction product was extracted with ethanol (20 mL) and purified by TLC ($CH_2Cl_2$:MeOH=10:1) to obtain coumarin-conjugated terpestacin (yield: 61%). The synthesized coumarin-conjugated terpestacin is depicted in Formula 4.

Figure 1:
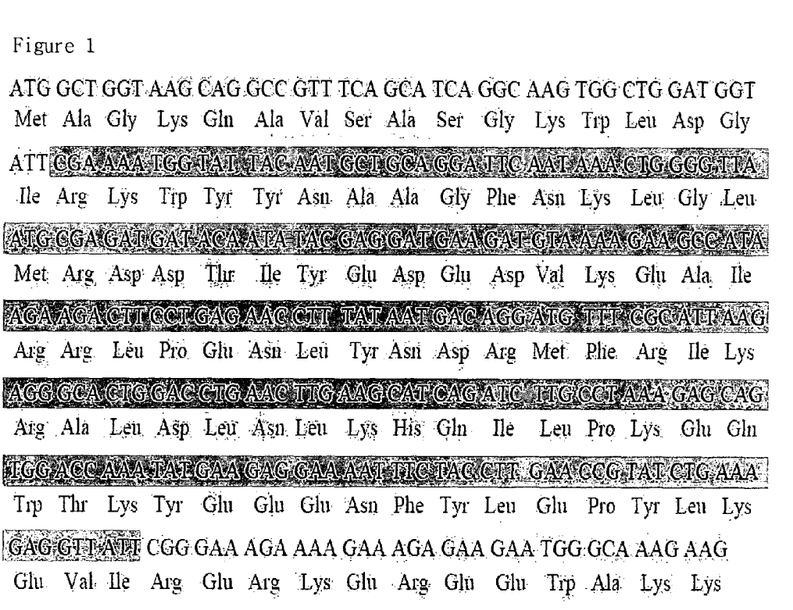
FIG. 1 depicts a phage-encoding sequence (SEQ ID NO: 1) of human QP-C in QP-C-expressing bacteriophage T7 (SEQ ID NO: 2). A gray box is a phage-encoding sequence (82 aa) of human QP-C.

MALDI-MS for $C_{49}H_{71}N_3O_9$ m/z 868.5 $[M+Na]^+$.

bound bacteriophage T7 particles. Terpestacin-bound bacteriophage T7 particles were elated for 1 hour with addition of terpestacin (100 μM) dissolved in TBS buffer. The elated bacteriophage T7 particles were infected into E. coli strain BLT5615 cultured on LB agar medium. The thus-formed bacteriophage T7 plaques were isolated and DNA sequences were analyzed to obtain bacteriophage expressing a ubiquinone-binding protein (QP-C) of the mitochondria complex III. A sequence of human QP-C encoded by bacteriophage T7 is set forth in FIG. 1.

Cloning, Expression and Purification of Human QP-C Protein

Using, liver tissue cDNA library as a template, a QP-C gene (GENBANK® Accession No. NM__006294 was amplified by polymerase chain reaction (PCR). Sequences of PCR primers used herein are as follows: forward primer 5'-ATGT-GAATTCATGGCATGGTAAGCAGGCC-3', and reverse primer 5'-ATGCCTCGAGCTTCTTTGCCCATTCTTC-3'. The QP-C gene was inserted into a multi cloning site (EcoRI/

(4)

Preparation of QP-C-expressing Bacteriophage T7

Figure 2:
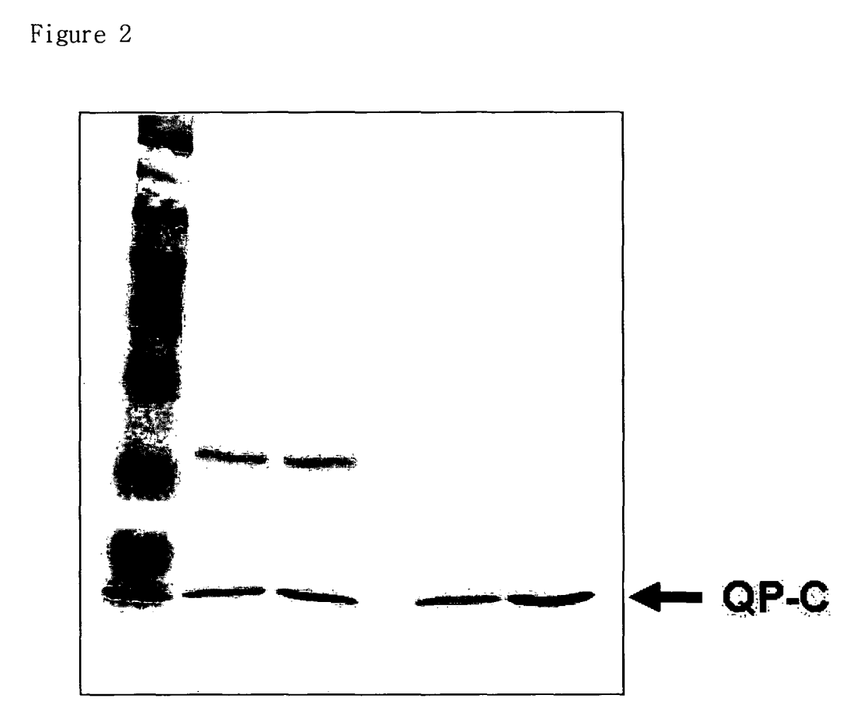
FIG. 2 is a micrograph of a protein electrophoretic pattern showing expression and purification results of a QP-C protein. The leftmost lane represents a size marker, and Lanes 1 through 4 respectively represent loading of a purified QP-C protein (Lanes 1 and 2: GST+QP-C, and Lanes 3 and 4: QP-C).

Bacteriophage T7 (NOVAGEN®) was purchased which encodes cDNA library obtained from live different human tissues (hepatoma, normal liver, dementia brain, normal brain, and normal stomach). A host cell E. coli BLT5615 was infected with Bacteriophage followed by amplification. Biotinylated terpestacin (5 μM) in TBS buffer (pH 7.5) was immobilized on a streptavidin-coated 96-well plate (Pierce Biotechnology), and then the amplified, bacteriophage T7 library (6×$1.0^9$ pfu/mL) was added to the terpestacin-immobilized wells. After being stirred at room temperature for 1 hour, bacteriophage T7 particles which were not hound to terpestacin were washed with TBS buffer to remove the non- XhoI site) of a pGEX-4T1 vector (Amersham Pharmacia) which was then transformed into E. coli BL21 for protein expression, IPTG (1 mM) was added to the LB culture $OD_{600}$=0.6) of the transformed bacteria, followed by shaking culture at 37° C. for 4 hours. The cells were disrupted using a sonicator and the expressed GST/QP-C fusion protein was purified by addition of glutathione agarose heads (SIGMA®). In order to remove a GST portion of the fusion protein, thrombin (Amersham Pharmacia) was added thereto at room temperature, followed by overnight stirring. Only the supernatant containing the QP-C protein was recovered by centrifugation (see FIG. 2).

Angiogenesis-inhibitory Activity of HDNT

1. Assay for Tube Formation of Human Umbilical Vein Endothelial Cells

A 48-well plate was coated with 150 μl of Matrigel (10 mg/mL, Collaborative Biomedical Products), followed by polymerization at 37° C. for 2 hours. Then, human umbilical vein endothelial cells (HUVECs, 1×10$^5$ cells/well) were inoculated on MATRIGEL®, to which VEGF (30 ng/mL, Upstate Biotechnology) and the inventive compound HDNT (2.5, 5 μM) were then added. The cells were cultured in an incubator for 8 hours while observing morphological changes of the cells under a microscope. Cytotoxicity of the compounds on tube-forming HUVECs evaluated by trypan blue staining (see FIG. 3).

2. HUVEC Invasion Assay

Invasion of human umbilical vein endothelial cells (HUVEC) was measured in vitro using a TRANSWELL® chamber system (Corning Costar) equipped with a polycarbonate filter. First, a lower part of the filter was coated with 10 μl of gelatin (10 mg/mL) for 1 hour, and an upper part of the filter was coated with 10 μl of MATRIGEL® (3 mg/mL) for 2 hours. Next, 600 μl of ERM-2 medium was added to the TRANSWELL®, to which VEGF (30 ng/mL) and the inventive compound HDNT (2.5, 5 μM) were then added. The coated filter was placed on the TRANSWELL®, and HUVECs (1×10$^5$ cells/well) were inoculated on the upper part of the filter, followed by cell culture in an incubator for 18 hours. Then, the cells were fixed with 70% methanol and stained with hematoxylin/eosin. Total cells in one filter were microscopically counted to measure a degree of cell invasion (see FIG. 4).

Regulatory Activity of HDNT on Mitochondrial Functions

1. Determination of Mitochondrial Membrane Potential

Human umbilical vein endothelial cells (HUVEC) were seeded on a 24-well plate (2×10$^4$ cells/well) and cultured in EBM-2 (LONZA®) medium containing 10% fetal bovine serum (INVITROGEN®). Then, the cells were washed with PBS buffer (pH 7.4) and the culture medium was then replaced with a fresh one. The inventive compound HDNT (1, 5, 10 μM) was added to the culture medium and the cells were incubated for 4 hours. In order to measure changes of the mitochondrial membrane potential, the cells were stained with 0.25 of a lipophilic cationic probe 5,5'6,6'-tetrachloro-1,1',3,3'-tetraethylbenzimidazole-carbocyanine iodide (JC-1, MOLECULAR PROBES®) for 15 min. The carbocyanine cationic dye forms a red fluorescent J-aggregate at a hyperpolarization membrane potential (to −140 mV), and the dye maintains a green fluorescent monomeric form at a depolarization membrane potential (to −100 mV). The stained cells were washed twice with PBS buffer. A microscopic image (×100) was obtained under an IX70 fluorescent microscope OLYMPUS®) (see FIG. 5).

2. Competitive Binding Assay by Phage Display

QP-C-expressing bacteriophage T7 was infected into a host cell E. coli BLT5615, followed by amplification. The inventive compound HDNT (200 μM) and the compound terpestacin (200 μM) binding to QP-C were each added to the culture (6×10$^9$ pfu/mL) of the amplified QP-C-expressing bacteriophage T7, followed by stirring at room temperature for 1 hour. Biotin and biotinylated terpestacin (5 μM), dissolved in TBS buffer (pH 7.5), were each immobilized on streptavidin-coated 96-well plates, and the reaction mixture solution of the QP-C phage and the compound was added to the biotinylated terpestacin-immobilized wells. Following stirring at room temperature for 1 hour, QP-C-expressing bacteriophage T7 particles not bound to the biotinylated terpestacin were washed three times with TBS buffer to remove non-bound phage particles. The QP-C-expressing bacteriophage T7 particles bound to the biotinylated terpestacin were eluted for 1 hour with addition of terpestacin (100 μM) dissolved in TBS buffer. The eluted QP-C-expressing bacteriophage T7 particles were infected into E. coli strain BLT5615 cultured on LB agar medium. The thus-formed bacteriophage plaques were counted and the results were compared between the treated group and the control group (see FIG. 6).

3. Competitive Binding Assay by Fluorescent Staining

Human umbilical vein endothelial cells (HUVEC) were seeded on a 24-well plate (2×10$^4$ cells/well) and cultured in EBM-2 (LONZA®) medium containing 10% fetal bovine serum (INVITROGEN®). Then, the cells were washed with PBS buffer (pH 7.4), and the culture medium was replaced with a fresh one. The inventive compound HDNT (10 μM) or the compound terpestacin (30 μM) binding to QP-C was added to each well and the cells were incubated for 24 hours. A fluorescent dye coumarin (20 μM) and coumarin-conjugated terpestacin (20 μM) were each added to the control group and the treated group, followed by incubation for another 2 hours. The cells were washed with PBS buffer. Fluorescent intensity was observed under an IX70 fluorescent microscope (OLYMPUS®) and a microscopic image was taken (see FIG. 7).

4. Competitive Binding Assay by Surface Plasmon Resonance

Biotin or biotinylated terpestacin (100 μM) was sequentially immobilized on flow cells of a streptavidin-coated sensor chip (BIACORE® AB). The inventive compound HDNT (25 μM) or the compound terpestacin (25 μM) binding to QP-C was added to HBS-EP buffer (pH 7.4, 10 mM HEPES, 150 mM NaCl, 3 mM EDTA) of the purified QP-C protein (25 μM) which was then poured on a surface of the sensor chip at a flow rate of 30 μl min.

The binding sensorgram containing association and dissociation curves was obtained by BIACORE® 2000, and 50 mM NaOH (5 μl) was poured on the sensor chip surface to result in regeneration. Herein, the binding sensorgam was obtained by deducting a biotin-QP-C protein binding curve from a binding curve between the biotinylated terpestacin and the QP-C protein. A surface plasmon resonance response curve was analyzed using BIACORE® Evaluations software, version 3.1 (see FIG. 8).

Experimental Results

Angiogenesis-Inhibitory Activity of HDNT

Figure 3:
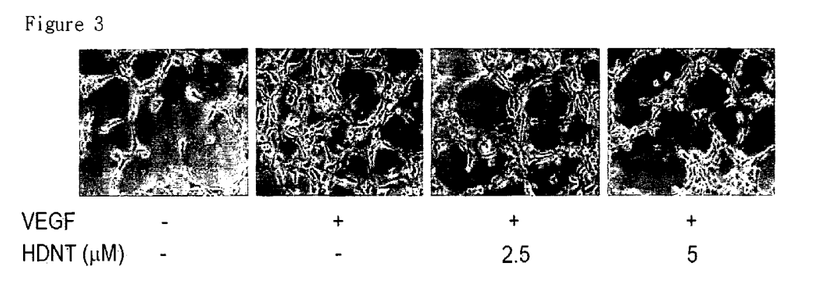
FIG. 3 is a micrograph of assay results for tube formation of human umbilical vein endothelial cells (HUVEC) upon treatment of HDNT. It can be seen that HDNT inhibits tube formation of HUVECs in a concentration-dependent manner.
Figure 4:
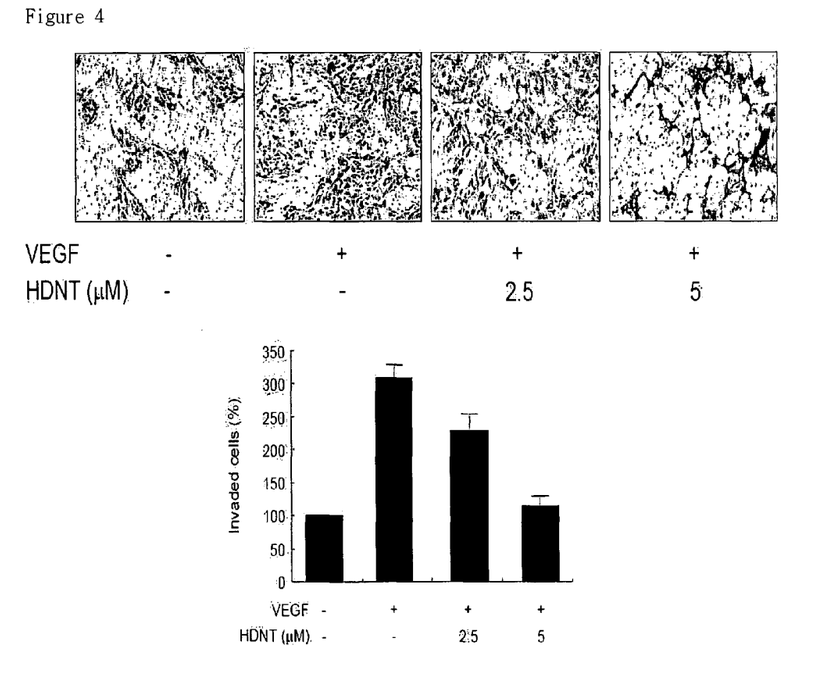
FIG. 4 is a micrograph showing assay results for invasion of human umbilical vein endothelial cells (HUVEC) upon treatment of HDNT. It can be seen that HDNT inhibits invasion of HUVECs in a concentration-dependent manner.

Angiogenesis is essential for a variety of physiological processes such as embryonic development, wound healing, and tissue or organ regeneration (Risau, W. 1994. Angiogenesis and endothelial cell function. *Arzneimittelforschung* 44: 416-417). However, continuous uncontrolled angiogenesis is pathogenically responsible for the occurrence of angiogenic diseases such as rheumatoid arthritis, diabetic retinopathy, solid tumor, hemangioma and psoriasis (Carmeliet, P. and R. K. Jain. 2000. Angiogenesis in cancer and other diseases. *Nature* 407: 249-257). Therefore, a novel anti-angiogenic compound of the present invention can be developed as therapeutic agents for angiogenesis-related cancers and other human diseases. In order to confirm whether the inventive compound HDNT exhibits anti-angiogenic activity, a representative in vitro angiogenesis assay, i.e. measurement of tube formation and invasion of HUVECs, was carried out. As shown in FIGS. 3 and 4, HDNT inhibited VEGF-mediated tube formation and invasion of HUVECs in a concentration-dependent manner. Further, from the fact that the cells where angiogenesis was inhibited by the compound of the present invention were not stained with trypan blue, it can be seen that anti-angiogenic activity of HDNT was not attributable to the cytotoxicity thereof. These results show that HDNT can be developed as a novel anti-angiogenic agent.

Determination of Mitochondrial Membrane Potential

Figure 5:
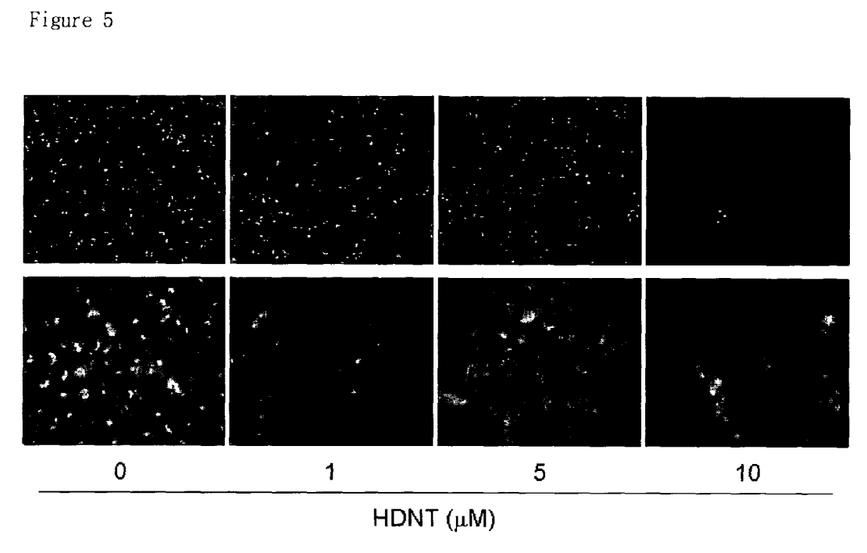
FIG. 5 is a fluorescence micrograph showing changes of the mitochondrial membrane potential upon treatment of HDNT. It can be seen that HDNT disrupts the mitochondrial membrane potential in a concentration-dependent manner.

With recent reports, it was revealed that mitochondrial dysfunction provides important pathogenic causes for chronic degenerative diseases such as cardiovascular diseases, diabetes and dementia, as well as carcinogenesis (3. Szewczyk, A. and L. Wojtczak. 2002. Mitochondria as a pharmacological target. *Pharmacol. Rev.* 54: 101-127). According to previous reports, it was known that production of reactive oxygen species (ROS) from the mitochondrial electron transfer system triggers angiogenesis essential for cancer metastasis and proliferation (Guzy, R. D., B. Hoyos, E. Robin, H. Chen, L. Liu, K. D. Mansfield, M. C. Simon, U. Hammerling, and P. T. Schumacker. 2005. Mitochondrial Complex III is required for hypoxia-induced ROS production and cellular oxygen sensing. *Cell Metab.* 1: 401-408). In order to examine whether anti-angiogenic activity of the inventive compound HDNT was due to regulation of the mitochondrial function, effects of HDNT on mitochondrial membrane potential changes of HUVECs were investigated. Changes in the mitochondrial membrane potential were measured using JC-1 that is a lipophilic cationic fluorescent marker. JC-1 forms a red fluorescent complex when the mitochondrial membrane potential is in a normal range (−140 mV), whereas it has a tendency to form a green fluorescent monomer when the mitochondrial membrane potential is disrupted (−100 mV). As shown in FIG. 5, the red fluorescence intensity becomes weak but the green fluorescence intensity becomes strong as a treatment concentration of HDNT increases. From these results, it can be seen that HDNT disrupts the mitochondrial membrane potential. Such results suggest that HDNT can modulate the mitochondrial function.

Competitive Binding Assay by Phage Display

Figure 6:
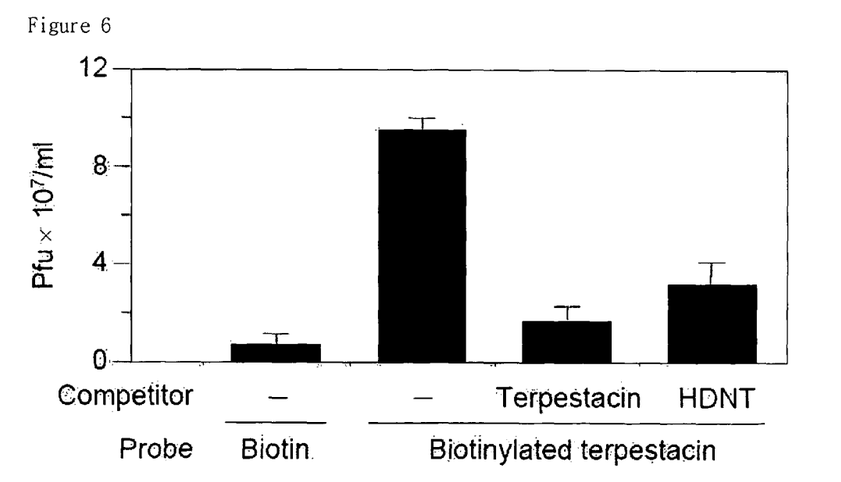
FIG. 6 graphically shows the results of phage display-based competitive binding assay upon treatment of HDNT. Whether binding of test compounds to QP-C-expressing bacteriophage T7 is competitive between HDNT and terpestacin was assayed. HDNT effectively inhibited the binding between biotin-terpestacin and QP-C-expressing bacteriophage T7. This result suggests that HDNT binds to a QP-C protein.

Terpestacin, a natural substance having anti-angiogenic activity, binds to QP-C to thereby inhibit production of mitochondrial reactive oxygen species (ROS). In order to confirm whether HDNT regulates the mitochondrial function through binding with QP-C, a phage display-based competitive binding assay was carried out using QP-C-expressing bacteriophage T7. As shown in FIG. 6, biotin did not bind to QP-C-expressing bacteriophage T7, whereas biotinylated terpestacin, the compound that binds to QP-C, specifically bound to QP-C-expressing bacteriophage T7. However, when an excess of terpestacin was first reacted with QP-C-expressing bacteriophage T7, the binding between the biotinylated terpestacin and the QP-C-expressing bacteriophage T7 was significantly inhibited by competitive binding. On the other hand, when HDNT was first reacted with QP-C-expressing bacteriophage T7, the binding between the biotinylated terpestacin and the QP-C-expressing bacteriophage T7 was effectively inhibited, similar to when terpestacin was first reacted. These results suggest that HDNT binds to the QP-C protein.

Competitive Binding Assay by Fluorescent Staining

Figure 7:
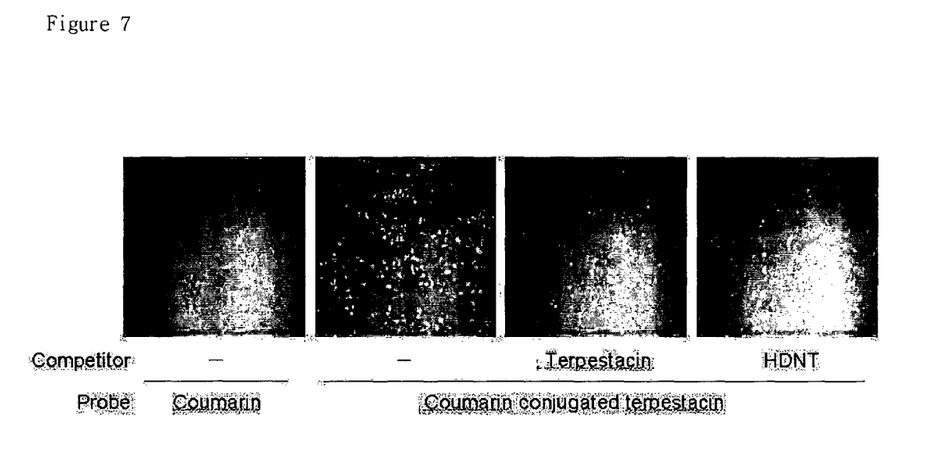
FIG. 7 shows the results of fluorescence staining-based competitive binding assay upon treatment of HDNT. HDNT exhibited effective inhibition of the binding between coumarin-terpestacin and QP-C.

In order to demonstrate that the inventive compound HDNT binds to QP-C, a competitive binding assay experiment was carried out using a fluorescent derivative of terpestacin, a known compound that binds to QP-C. As shown in FIG. 7, treatment of HUVECs with coumarin-terpestacin resulted in intense blue fluorescence in the cytoplasm where mitochondria are present, unlike coumarin treatment. When the cells were first treated with terpestacin before treatment with coumarin-terpestacin, the binding between the coumarin-terpestacin and the mitochondrial protein QP-C was inhibited by competitive binding, thus resulting in significant attenuation of blue fluorescence in the cytoplasm. On the other hand, when the cells were first treated with HDNT, blue fluorescence was significantly decreased similar to first treatment with terpestacin, thus confirming that HDNT binds to QP-C.

Competitive Binding Assay by Surface Plasmon Resonance

Figure 8:
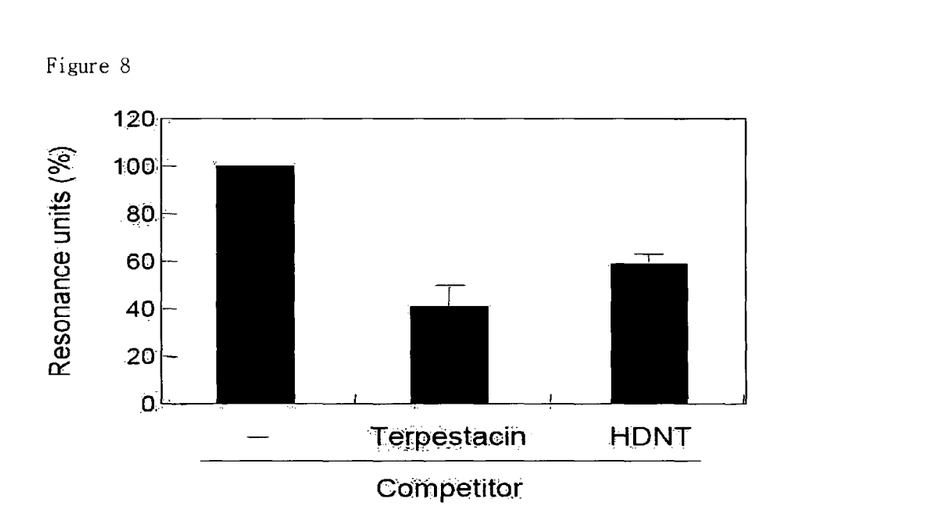
FIG. 8 graphically shows the results of surface plasmon resonance-based competitive binding assay upon treatment of HDNT.

In order to further demonstrate that the inventive compound HDNT binds to QP-C, a competitive binding assay experiment was carried out using a surface plasmon resonance technique that is capable of confirming direct binding of biological substances on the real-time basis, through the measurement of changes in a refractive index. When biotin and biotin-terpestacin were sequentially immobilized on flow cells of a streptavidin-coated sensor chip and then a reaction mixture of terpestacin and QP-C protein was then poured on a surface of the sensor chip, up to 60% of the binding between the biotin-terpestacin and the QP-C protein was inhibited by competitive binding (FIG. 8). On the other hand, when a reaction mixture of HDNT and QP-C protein was poured on a surface of the sensor chip, the binding between the biotin-terpestacin and the QP-C protein was inhibited by 40%, similar to the results obtained upon terpestacin treatment. These results demonstrate that HDNT directly binds to QP-C.

According to the above experimental results, it can be seen that the compound of the present invention, i.e. HDNT, selectively targets the mitochondrial protein QP-C to thereby regulate the mitochondrial function. Therefore, HDNT can be developed as therapeutic agents for treatment of angiogenic diseases including cancers.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

The compounds used as an active ingredient in the pharmaceutical composition of the present invention bind to QP-C to provide effective prevention of angiogenesis and can be effectively used for prevention and/or treatment of angiogenesis-related diseases or disorders. Further, the active compounds of the present invention inhibit biological functions of QP-C, which consequently leads to inhibition of angiogenic responses without the risk of cellular apoptosis, thus significantly improving safety of the drug.

The invention claimed is:

1. A pharmaceutical composition for treating angiogenesis, comprising:
(a) a therapeutically effective amount of an inhibitor of ubiquinone-binding protein (QP-C) of mitochondrial complex III represented by a compound of Formula 1:

(1)

wherein $R_1$ to $R_{12}$ are each independently hydrogen, halo, hydroxy, cyano, amino, nitro, nitroso, carboxyl, $C_1$-$C_{12}$ alkyl, $C_2$-$C_6$ alkenyl, $C_3$-$C_8$ cycloalkyl, $C_5$-$C_7$ cycloalkenyl, $C_1$-$C_6$ alkylamino, alkoxy, aryl, heteroaryl, arylalkyl, arylalkenyl or alkylaryl; $R_{13}$ is hydrogen, hydroxy, $C_1$-$C_{12}$ alkyl or $C_1$-$C_6$ alkoxy; and X is oxygen or sulfur; and
(b) a pharmaceutically acceptable carrier.

2. The composition according to claim 1, wherein $R_1$ is hydrogen, hydroxy, $C_{12}$ alkyl or $C_1$-$C_6$ alkoxy.

3. The composition according to claim 1, wherein $R_2$ to $R_{12}$ are each independently hydrogen, hydroxy, $C_1$-$C_{12}$ alkyl, or $C_1$-$C_6$ alkoxy.

4. The composition according to claim 1, wherein $R_{13}$ is hydrogen or hydroxy.

5. The composition according to claim 1, wherein X is oxygen.

6. The composition according to claim 1, wherein $R_1$ is hydroxy, $R_2$ to $R_{12}$ are each independently hydrogen, $R_{13}$ is hydrogen and X is oxygen.

7. A pharmaceutical composition for inhibiting ubiquinone-binding protein (QP-C) of mitochondrial complex III comprising:

(a) a therapeutically effective amount of a compound of Formula 1:

(1)

wherein $R_1$ to $R_{12}$ are each independently hydrogen, halo, hydroxy, cyano, amino, nitro, nitroso, carboxyl, $C_1$-$C_{12}$ alkyl, $C_2$-$C_6$ alkenyl, $C_3$-$C_8$ cycloalkyl, $C_5$-$C_7$ cycloalkenyl, $C_1$-$C_6$ alkylamino, $C_1$-$C_6$ alkoxy, aryl, heteroaryl, arylalkyl, arylalkenyl or alkylaryl; $R_{13}$ is hydrogen, hydroxy, $C_1$-$C_{12}$ alkyl or $C_1$-$C_6$ alkoxy; and X is oxygen or sulfur; and (c) a pharmaceutically acceptable carrier.

* * * * *

UNITED STATES PATENT AND TRADEMARK OFFICE
CERTIFICATE OF CORRECTION

PATENT NO. : 8,450,502 B2
APPLICATION NO. : 12/865356
DATED : May 28, 2013
INVENTOR(S) : Kwon et al.

Page 1 of 1

It is certified that error appears in the above-identified patent and that said Letters Patent is hereby corrected as shown below:

In the Claims:

Column 16,
Line 46, "arc" should read --are--;
Line 49, "alkoxy" should read --$C_1$-$C_6$ alkoxy--;
Line 55, "$C_{12}$ alkyl" should read --$C_1$-$C_{12}$ aklyl--.

Column 17,
Line 20, "arc" should read --are--.

Signed and Sealed this
Third Day of September, 2013

Teresa Stanek Rea
*Acting Director of the United States Patent and Trademark Office*